(12) United States Patent
Mitchell et al.

(10) Patent No.: US 11,383,069 B2
(45) Date of Patent: Jul. 12, 2022

(54) SAFETY DEVICE FOR RETRACTION OF A NEEDLE AND GUIDEWIRE FOR MEDICAL PROCEDURES AND METHOD OF USE

(71) Applicant: REDSMITH, INC., Walnut Creek, CA (US)

(72) Inventors: James D. Mitchell, Walnut Creek, CA (US); Andrew A. Thoreson, Long Lake, MN (US)

(73) Assignee: REDSMITH, INC., Walnut Creek, CA (US)

( * ) Notice: Subject to any disclaimer, the term of this patent is extended or adjusted under 35 U.S.C. 154(b) by 142 days.

(21) Appl. No.: 16/682,849

(22) Filed: Nov. 13, 2019

(65) Prior Publication Data
US 2020/0078566 A1    Mar. 12, 2020

Related U.S. Application Data

(63) Continuation of application No. PCT/US2018/032474, filed on May 12, 2018.

(60) Provisional application No. 62/567,470, filed on Oct. 3, 2017, provisional application No. 62/505,902, filed on May 13, 2017.

(51) Int. Cl.
*A61M 25/06* (2006.01)
*A61M 25/09* (2006.01)

(52) U.S. Cl.
CPC .... *A61M 25/0631* (2013.01); *A61M 25/0606* (2013.01); *A61M 25/09041* (2013.01)

(58) Field of Classification Search
CPC ............. A61M 5/3232; A61M 5/3234; A61M 5/3245; A61M 5/321; A61M 25/0631; A61M 25/0606; A61M 25/06; A61M 25/09041; A61M 25/0637; A61M 25/0612; A61M 25/0113; A61M 2205/273; A61M 2025/09116; A61M 2025/09125

See application file for complete search history.

(56) References Cited

U.S. PATENT DOCUMENTS

| | | | |
|---|---|---|---|
| 5,704,914 A | 1/1998 | Stocking | |
| 6,547,762 B1 | 4/2003 | Botich | |
| 2004/0186426 A1 | 9/2004 | Allard | |
| 2010/0094310 A1* | 4/2010 | Warring | ............ A61M 25/0606 606/108 |
| 2010/0210934 A1 | 8/2010 | Belson | |
| 2016/0015945 A1 | 1/2016 | Warring | |
| 2020/0001051 A1* | 1/2020 | Huang | ................. A61M 25/06 |

* cited by examiner

*Primary Examiner* — Tiffany Legette
*Assistant Examiner* — Antarius S Daniel
(74) *Attorney, Agent, or Firm* — Rachel H. Huffstetler; FisherBroyles, LLP

(57) ABSTRACT

The medical safety device utilizes an active needle retraction assembly and a guidewire retraction assembly which retracts the guidewire at a retraction rate greater than the needle retraction rate to safely manage significant lengths of guidewire. A passive retraction system may be used with the active retraction assembly to rapidly retract the needle and guidewire after initial retraction. The guidewire retraction assembly includes a pulley system to increase forces applied to the device to retract the guidewire and needle retraction assembly retracts the needle. The device encloses the needle and guidewire to protect from contact with contaminated materials.

17 Claims, 23 Drawing Sheets

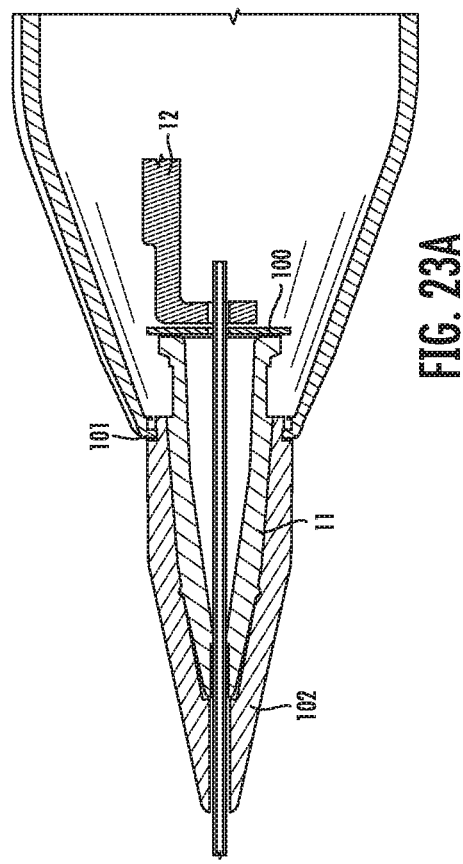
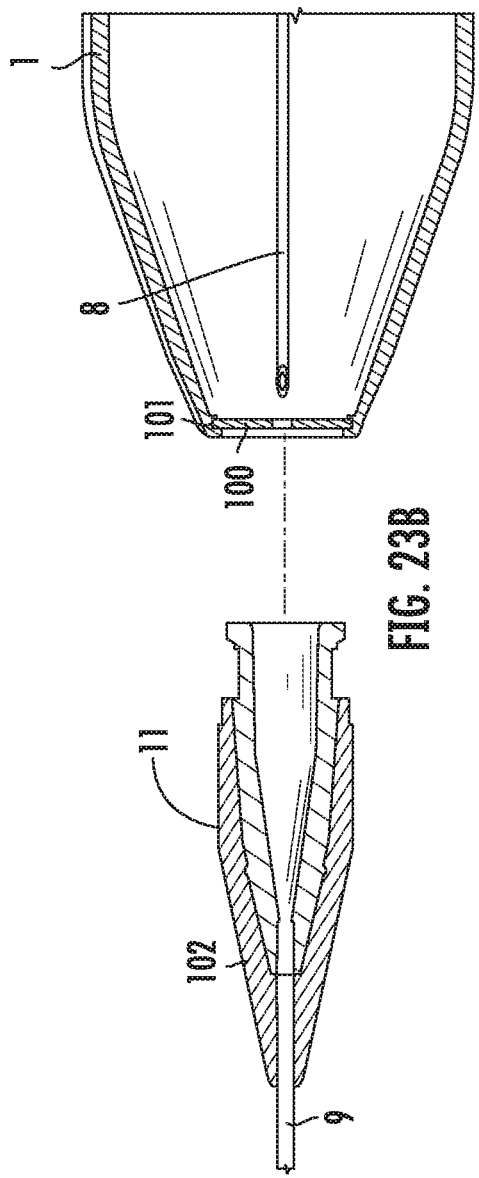

SAFETY DEVICE FOR RETRACTION OF A NEEDLE AND GUIDEWIRE FOR MEDICAL PROCEDURES AND METHOD OF USE

CROSS-REFERENCE TO RELATED APPLICATIONS

The present invention is a continuation of International Application No. PCT/US2018/032474, filed May 18, 2018, which claims the benefit of priority to U.S. Provisional Application No. 62/505,902, filed May 13, 2017, and to U.S. Provisional Application No. 62/567,470, filed Oct. 3, 2017, each of which is incorporated by reference in their entirety.

FIELD OF THE INVENTION

The present invention is directed, generally, to safety devices used in connection with medical devices for providing intravascular access into a blood vessel, including veins, arteries, or other anatomical structure. More specifically, the safety device allows for simultaneous retraction of both a needle and guidewire, both of which are likely contaminated after a medical procedure. The invention allows for both active and passive retraction into a protective housing to minimize the risk of injury or infection to the user.

BACKGROUND OF THE INVENTION

Catheters are currently used for several medical purposes. Many catheters are designed for endovascular use, including vascular access and minimally invasive vascular interventions. However, catheters may also be used to access any anatomic cavity including, but not limited to the thorax, abdomen, retroperitoneum, and/or pelvis. Sharp needles are required to traverse the skin and other tissues of the body to gain access into the anatomic target. Additionally, flexible guidewires are often used to assist placement of a catheter into a body cavity. An exemplary procedure includes placement of a peripheral or midline (extended-dwell) catheter over an integrated needle and guidewire device.

Once the needle and guidewire have traversed the skin and contact the patient's tissues and bodily fluids, both components pose a risk to healthcare workers. Bloodborne and fluid borne pathogens remain on the needle and/or guidewire after both have been removed from the patient following insertion of a catheter or other tubular member. Until properly disposed within a biohazard sharps container, these devices carry a risk of infecting the healthcare worker through many established modes of transmission. Furthermore, these devices could contaminate other nearby surfaces, equipment, and other fomites, which could, in turn, transmit infections to other patients through hospital acquired (or associated) infections (HAIs). These HAIs are of paramount concern to healthcare facilities and are recognized as a serious cause of morbidity and mortality.

To mitigate this risk, several devices have been designed and marketed with the purpose of either active or passive safety mechanisms designed to protect healthcare workers from the sharp end of a needle. For clarity, it is to be understood that the word "active", refers to such instrument that requires a user to actively actuate the device through much of the safety mechanism cycle. It is to be understood that the word "passive," refers to such instrument that only requires a user to only initiate the cycle of the safety mechanism; after which the device performs much of the safety mechanism cycle to its completion. Either of these mechanisms, active or passive, taken singularly, have certain limitations.

Many devices with integrated safety components are cumbersome to use, which may interfere with the ease of use of a particular device, or may even increase the risk of improper catheter placement. In others, once the safety mechanism is triggered, it is no longer possible to revert to the original configuration, and therefore the needle is no longer available if needed for a subsequent portion of the procedure. Finally, contemporary safety devices are either only active or only passive in their mechanism, and none to our knowledge, incorporate the benefits of both instruments.

Importantly, none of the existing devices in the art contain a means of also retracting a contaminated guidewire. Various devices have been created to promote so-called "bloodless systems", for instance, to prevent any blood from contaminating nearby surfaces, including the patient's own skin (which may be a vector of contamination between healthcare providers and patients). However, none have focused on containing a substantial length of contaminated, and highly mobile, guidewire. If used in placement of a catheter, a guidewire is certainly contaminated with blood, either macroscopically, or via small amounts disposed along the wire surface that harbor microscopic bacteria or virions. Although most guidewires are not sharp enough to puncture the skin or a protective glove or garment, the contaminates from a guidewire could inadvertently contact a healthcare worker's mucous membranes, including but not limited to nasal, oral, and pharyngeal mucosae, and conjunctivae. Any unprotected areas of broken skin could represent an additional rout of infection originating from a contaminated guidewire in a healthcare worker. Any surface touched by the contaminated guidewire poses a risk to all individuals, including other patients in the clinic or hospital setting, many of whom are of compromised health.

As such, an optimal safety device would include a mechanism for protecting anyone in the healthcare setting from both a contaminated needle as well as a contaminated guidewire.

SUMMARY OF THE INVENTION

The present invention overcomes shortcomings of current devices by allowing for single hand operation of a safety device that provides full retraction of the vascular access needle and its accompanying guidewire. The needle safety device is envisioned to be used in conjunction with a vascular access catheter such as a peripheral IV, midline catheter or extended-dwell peripheral IV (EDPIV), central venous catheter (CVC), or arterial access catheter ("art-line"), but in practice could be used in conjunction with any medical device that contains a sharp needle for puncturing the skin. In one embodiment, the device uses a combination of a slide tab mechanism and a compression spring to utilize both active and passive retraction of both the needle and guidewire.

It is understood that the following description of the safety device with use of such integrated vascular access system is exemplary, and neither limiting in the safety device scope, its application, components, or subassemblies, with respect to its value in many other vascular access devices, known in the art, or yet to be known. Additionally, the invention described here is not limited to medical devices used for vascular access, but could be applied to any manner of inserting a catheter over a needle and guidewire into the body. Exemplary devices including nephrostomy tubes, peritoneal dialysis catheters, abscess drains, paracentesis catheters, chest tubes, and biliary drains.

The device comprises a housing having upper and lower components. In the initial configuration, a needle retainer is positioned adjacent the distal end of the housing wherein the sharp needle tip extends beyond the distal end of the housing. Disposed longitudinally within the central lumen of the needle is a guidewire used to assist in vascular access. The safety device described herein is to be used after the guidewire and access catheter have been deployed. Although the safety device described herein is envisioned to be used with a vascular access catheter, it is within the scope of this invention to be used with any medical needle used to puncture the skin and gain access within the body.

The housing defines a longitudinally extending channel and a tab extends upwardly through the channel. As shown and described, the tab, shown and described as a finger slide extends from and moves along the top surface of the housing, it is within the scope of the invention to have the slide tab on any surface of the housing. This tab is rigidly connected to a retraction frame.

The retraction frame extends longitudinally, from a proximal to distal end. Its proximal end defines an aperture configured for receipt and sliding passage of a guidewire. A pulley system for advancing or retracting the guidewire is positioned between the retraction frame ends and is used to retract the guidewire. The guidewire pulley system contains a guidewire drive (or retraction) pulley and a second guidewire tension pulley. The surfaces of the two pulleys are in physical contact with each other, and they are contained within the frame via pins that allow rotation. Adjacent pulley surfaces contain a groove within which the guidewire slidably passes. The guidewire drive pulley also comprises a gear disposed on one side, functioning as a compound gear. The geared portion of the compound gears cooperates with a gear rack positioned within a lower rail insert of the housing. This gear facilitates rotation of the drive as the frame proximally advances by movement of the slide tab. This drive pulley rotation retracts the guidewire, and the predetermined ratio of the diameter of the gear to that of the pulley defines the speed at which the guidewire is retracted. It is within the scope of this invention to have the guidewire retract at a rate of two to three times or more compared to the frame and finger slide. This minimizes the user's finger translation needed to create some proportionately larger amount of guidewire retraction for better ease of use.

The longitudinal configuration of the retraction frame defines a cavity between its distal and proximal ends for housing the pulley system. A clasp for retracting the needle is also provided. When the frame is in the fully advanced position, the clasp engages a needle retainer. Any sliding forces applied to the slide tab will be transmitted to the frame which is engaged with the needle retainer, thus retracting the needle in combination with the frame.

A needle retainer clasp is also provided in the distal portion of the lower rail insert. The clasp holds the needle in place until the user fully advances the retraction frame through actuation of the slide tab. When the frame is in the fully advanced position, the drive pully contacts and depresses the needle retainer clasp. This frees the needle to be retracted in conjunction with the frame.

Once the slide tab and retraction frame have been actively pulled proximally a sufficient distance to retract most of the guidewire into the needle, a passive, spring loaded retraction mechanism is engaged. It should be noted here that it is a useful aspect to have the wire mostly constrained within the needle, but still partially beyond the needle tip. At this point of transition between active and passive retraction phases, the wire continues to obturate the needle tip and prevent needle stick injury while it may still extend beyond the distal housing. Next, a curvilinear, tubular space defined by the lower rail insert and the wall of the lower housing constrains a compression spring. A safety shuttle conduit creates a passage to receive the spring and safety shuttle. The spring and safety shuttle are held in place under static force by a safety trigger.

As the retraction frame is actuated proximally, a series of movements are initiated. Specifically, the side trigger tab of the retraction frame engages with the body of the safety shuttle as it slidably courses over a depressed shuttle tab. The retraction frame and spring-loaded safety shuttle body are now joined as the first part of the passive retraction phase. Next, very slight retraction causes the side trigger tab to laterally displace the trigger latch such that an inferior projection of the trigger latch frees the safety shuttle; the system is now effectively armed with one additional step. Finally, a tab in the upper housing strips the finger slide from the retraction frame leaving the components of the retraction frame and safety shuttle system joined, but substantially disengaged from all other restraining structures. These remaining components, carrying the contaminated needle and wire, are rapidly pushed into the proximal device housing by the compression spring, and the components become substantially permanently encapsulated in the rigid housing.

An alternative aspect eliminates the passive component of retraction, and allows for complete active retraction controlled by the user. On the undersurface of the longitudinal member of the retraction frame is a rack that communicates with a compound gear also housed within the frame. This compound gear also communicates with a longitudinally oriented rack that is contained within the lower rail insert. When the frame is retracted through the more distal portion of the housing that does not contain this longitudinally oriented rack, the frame and the slide tab move in synchrony with about a 1:1 distance ratio. When the rack reaches the portion of the housing that contains the longitudinally oriented rack, the compound gear engages and the frame is retracted at a rate that is greater than that of the slide tab. The ratio of retraction rate will depend on the ratio of diameters of the compound gear. This feature allows the needle and guidewire to be retracted quickly once the guidewire has been retracted mostly within the needle and the housing, preventing spraying of bodily fluids from the guidewire. Once the slide tab reaches the fully retracted position, the needle and guidewire are both completely and securely contained within the housing, preventing physical contact with the user.

BRIEF DESCRIPTION OF THE DRAWINGS

FIG. 23A is a side partially broken away view of the distal tip of the needle safety device prior to detachment of the distal tip; and FIG. 23B is a side partially broken away view of the distal tip after detachment and closure of the end of the device with the needle retracted therein.

DETAILED DESCRIPTION OF THE INVENTION

The present invention will now be described in detail hereinafter by reference to the accompanying drawings. The invention is not intended to be limited to the embodiments described; rather, this detailed description is provided to enable any person skilled in the art to make and practice the invention.

As used herein, the terms "proximal" and "distal" are used to refer to the axial ends of the safety device, catheter, and various components. The term "proximal end" refers to the end closely adjacent the user of the assembly and the term "distal end" refers to the end of the catheter assembly that is percutaneously inserted into the patient, i.e., adjacent the needle tip. Also, as used herein, the "axial direction" refers to the longitudinal axis of the component or device from the proximal end to the distal end. The term "transverse" direction refers to a direction which intersects the longitudinal axis, at any angle.

The components of the safety device described herein are contained within a longitudinally oriented protective housing 1. Shown here, the device housing 1 comprises two upper components, the proximal upper housing 2 and distal upper housing 3, and a lower housing 4. However, it is within the scope of the invention for the housing to be made of more or fewer individual components, or arranged in an orientation other than one of a predominantly longitudinal or linear configuration. Additionally, the housing is envisioned to be made of medical grade plastic, but could be manufactured from any sterile material of robust composition to prevent needle injury.

Figure 1:
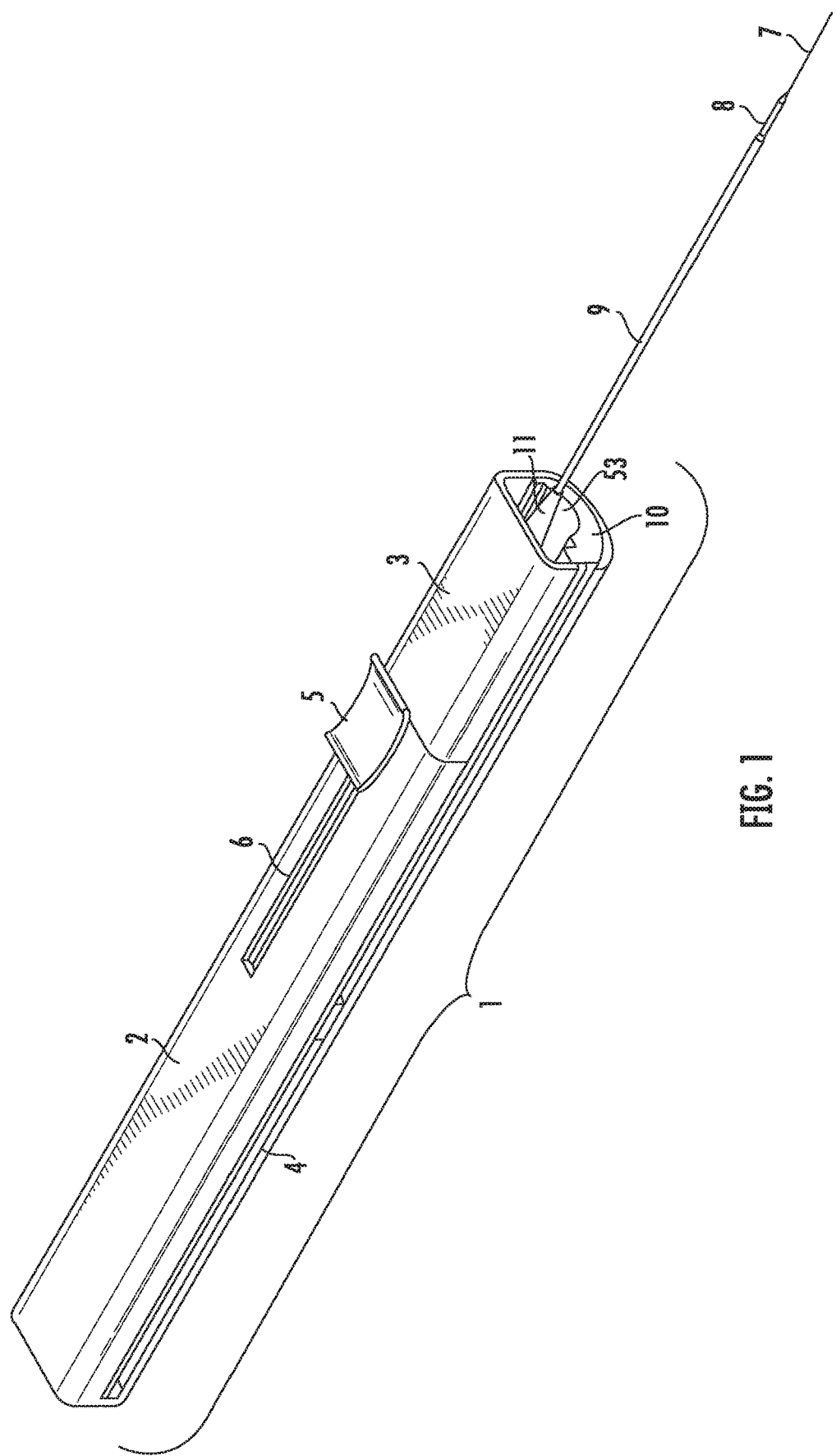
FIG. 1 is a perspective view of a vascular access catheter containing needle safety device with slide tab and guide wire in the advanced position.
Figure 2:
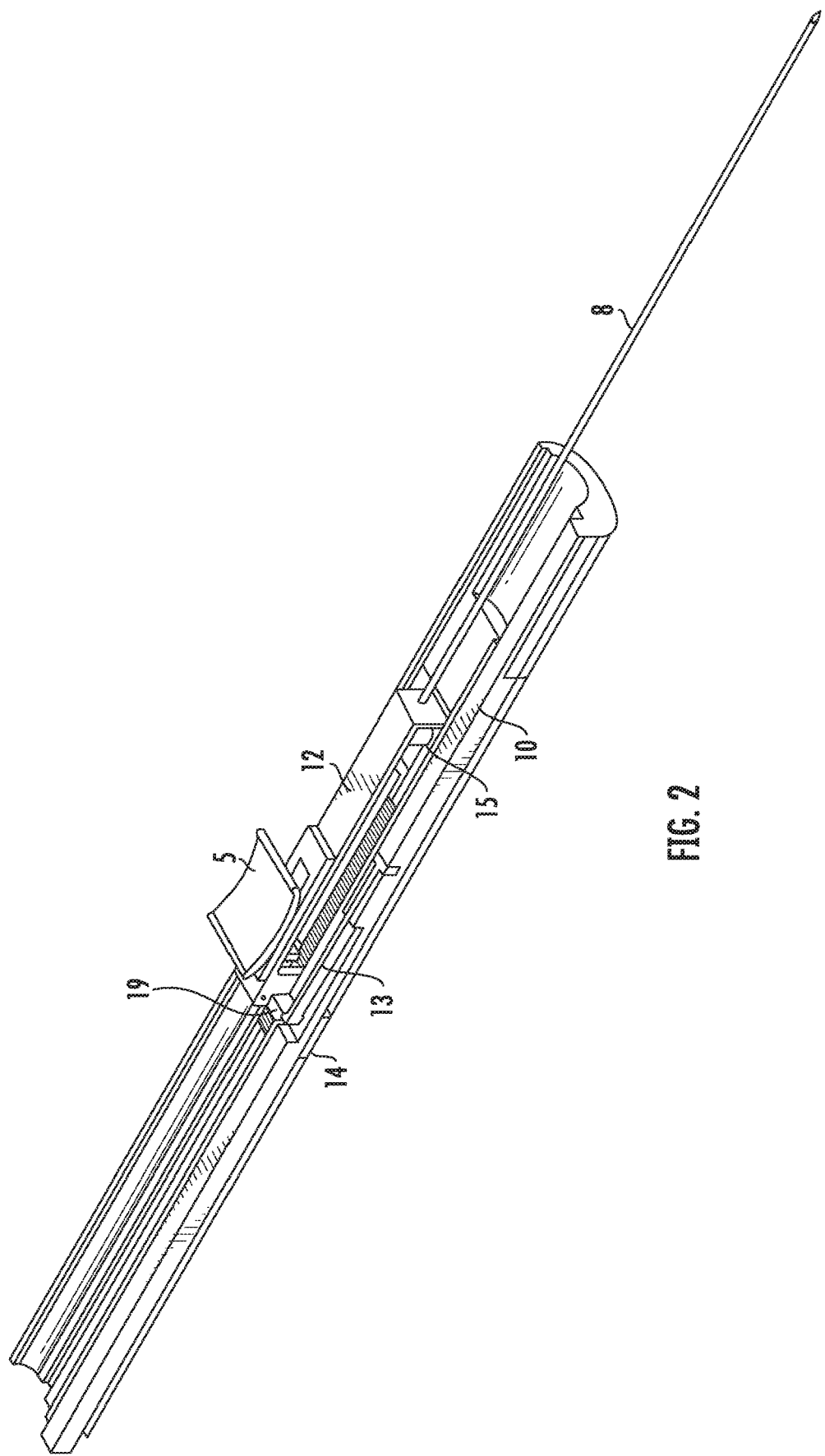
FIG. 2 is a perspective, partially broken away view of the lower housing and frame of the needle safety device in the starting position.

As shown in FIGS. 1 and 2, defined by the proximal upper housing 2 is a longitudinal housing slot 6 that allows receipt of an external tab shown in the form of a finger slide 5. The housing slot 6 allows proximal and distal translation of the finger slide 5, which then actuates the inner mechanics as described below. The finger slide 5 is slidably disposed within the housing slot 6, such that the distal extent of the housing slot is favored to be formed by the junctions of the proximal and distal upper housing 2 and 3. Although, it is within the scope of the present invention to be a housing slot 6 of potentially several different lengths or positions relative to the housing pieces. The most distal end of the housing contains an opening 53 through which passes the needle 8, catheter 9, and guidewire 7 complex.

The needle, catheter, and guidewire assembly comprises a hollow, sharp tipped medical needle 8 and a flexible guidewire 7 longitudinally and coaxially extending within the central lumen of the needle 8. The guidewire 7 is to be made of medical grade nitinol or similar material that allows flexibility without memory that can lead to bending or kinking of the guidewire. A medical catheter 9 is positioned over the needle 8 and guidewire 7. The catheter 9 will generally contain a proximal catheter hub 11, and cap 20 to prevent blood loss through the catheter hub 11 during insertion. See FIG. 5. According to one aspect, the device is used with a vascular access catheter such as a peripheral IV, midline extended dwell IV, arterial catheter, or central venous catheter. However, it is within the scope of this invention to be used with other medical catheters used to access body cavities including but not limited to nephrostomy tubes, abscess and other surgical drains, chest tubes, and biliary drains. These catheters are generally made of polyurethane or other biocompatible flexible polymers. For the purposes of this safety device, the finger slide 5 is used to retract the needle 8 and guidewire 7 once the catheter has been deployed as outlined below.

As shown in various Figures, including FIGS. 2-6, 9 and 11, within the central cavity of the protective housing 1, is a needle retraction assembly including a retraction frame 12, a lower rail insert 10, a needle retainer or hub 15 for retaining the needle 8 and a guidewire retraction assembly including a pulley assembly having a retraction pulley 22 and a tension pulley 34. The safety medical assembly further includes a safety trigger 13, a compression spring 28, and a safety shuttle 14 as a part of the guidewire retraction assembly according to one aspect of the invention.

Figure 8:
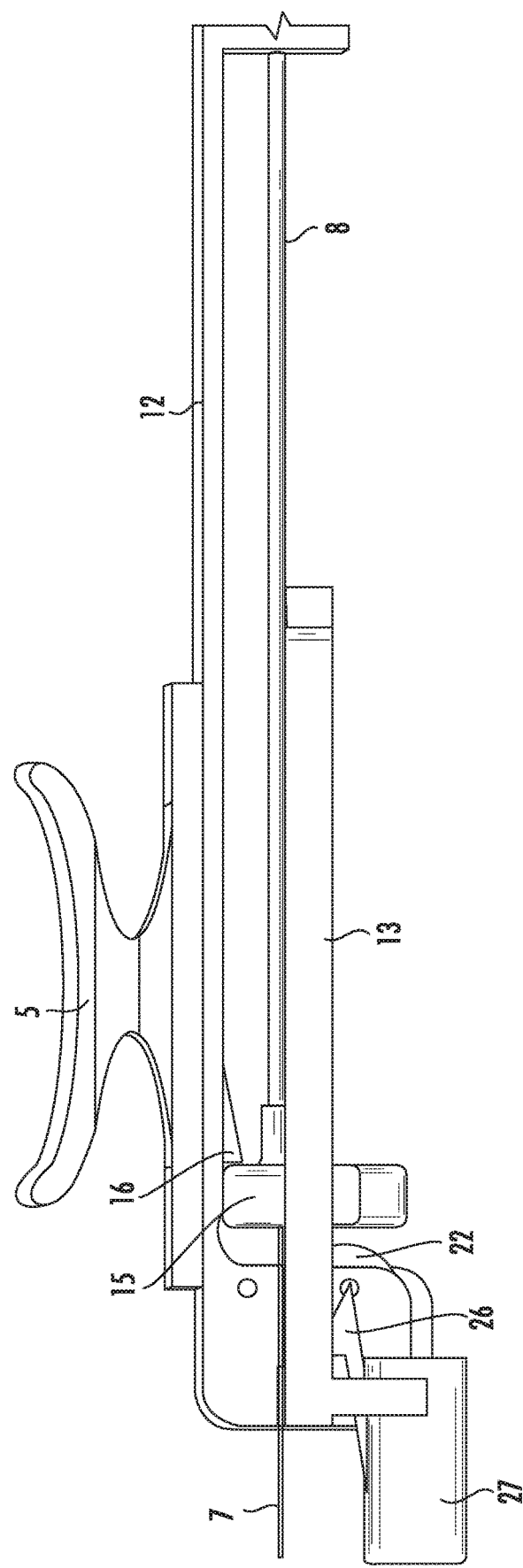
FIG. 8 is a side elevational, view of portions of the spring-loaded safety mechanism.
Figure 11:
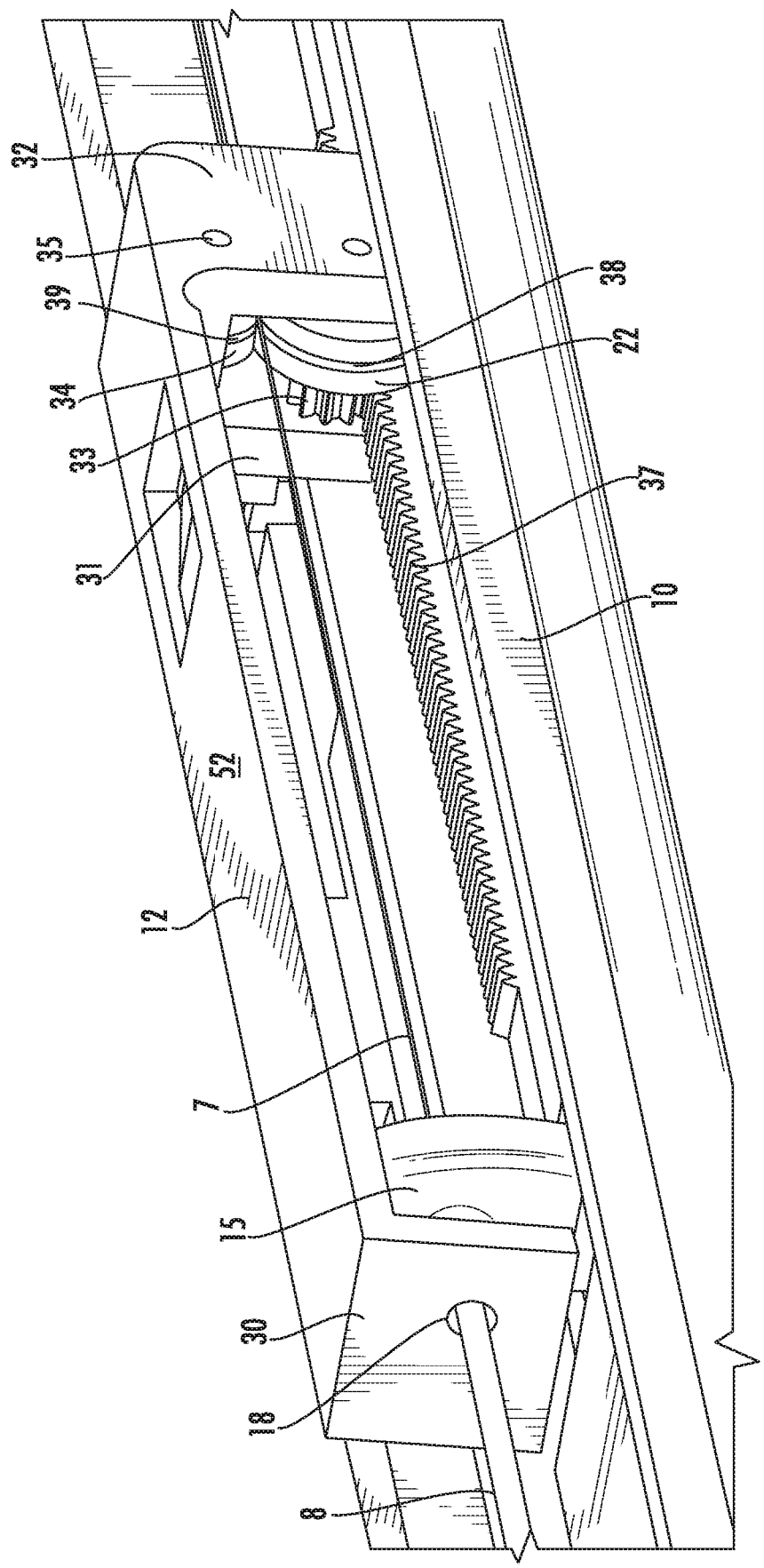
FIG. 11 is an enlarged, partially broken away, perspective view of the safety device showing the retraction frame and pulley system.
Figure 12:
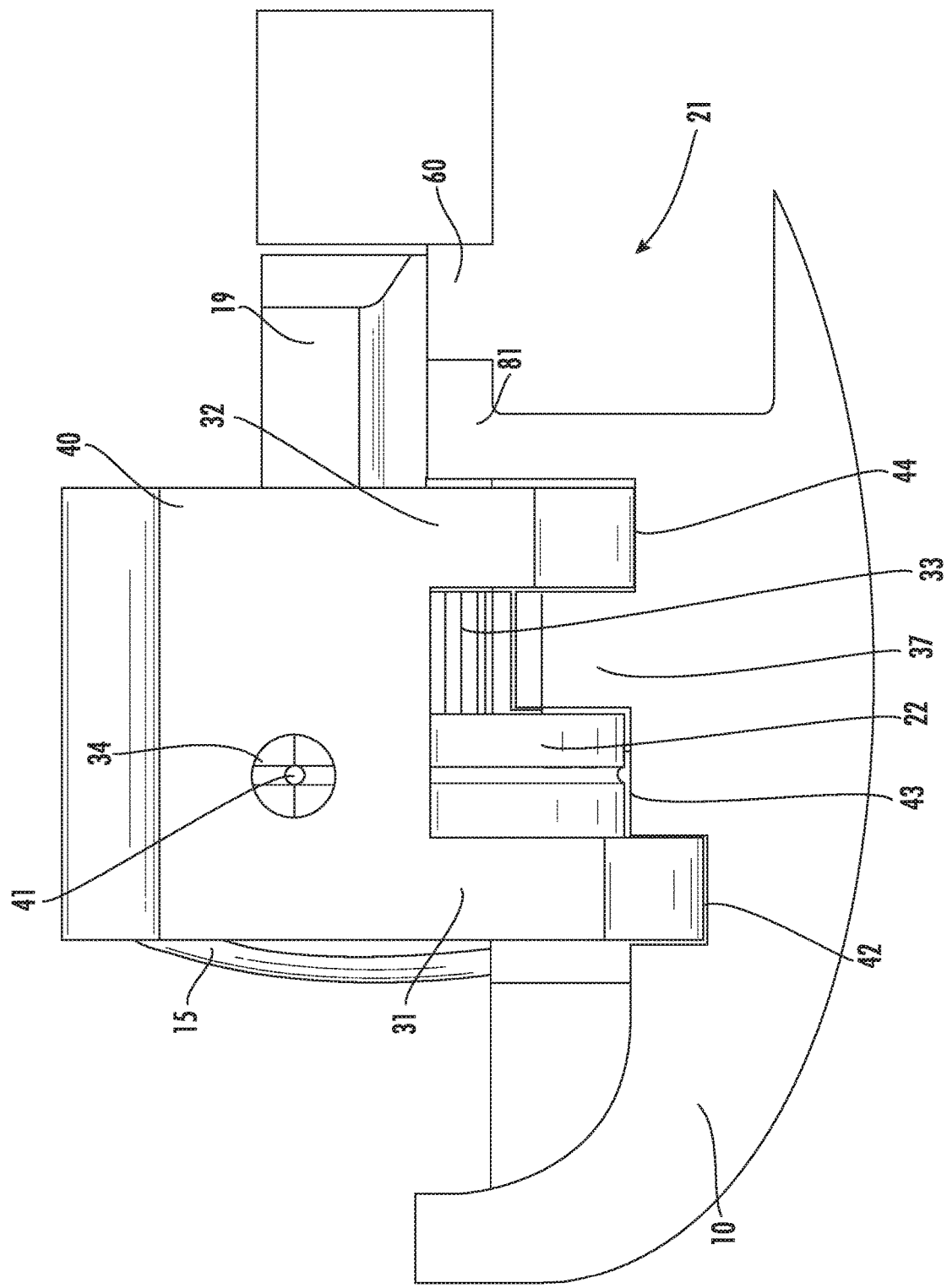
FIG. 12 is an enlarged, partially broken away, end view showing the orientation of the retraction frame and pully system with the lower rail insert.

The retraction frame 12 is in substantially rigid communication with the finger slide 5. See FIG. 8. Therefore, any proximal or distal motion of the finger slide 5 is transferred to the retraction frame 12. As shown in FIG. 11, the distal transverse surface 30 of the retraction frame 12 has an aperture 18 for receipt of the needle 8. As shown in FIG. 12, the proximal transverse surface 40 of the retraction frame 12 contains an aperture 34 for receipt of the guidewire 7. Extending below the proximal transverse surface 30 of the retraction frame 12 are two support struts 31 and 32. These support struts rest in and travel on respective longitudinally oriented channels 42 and 44 in the lower rail insert 10.

Figure 16:
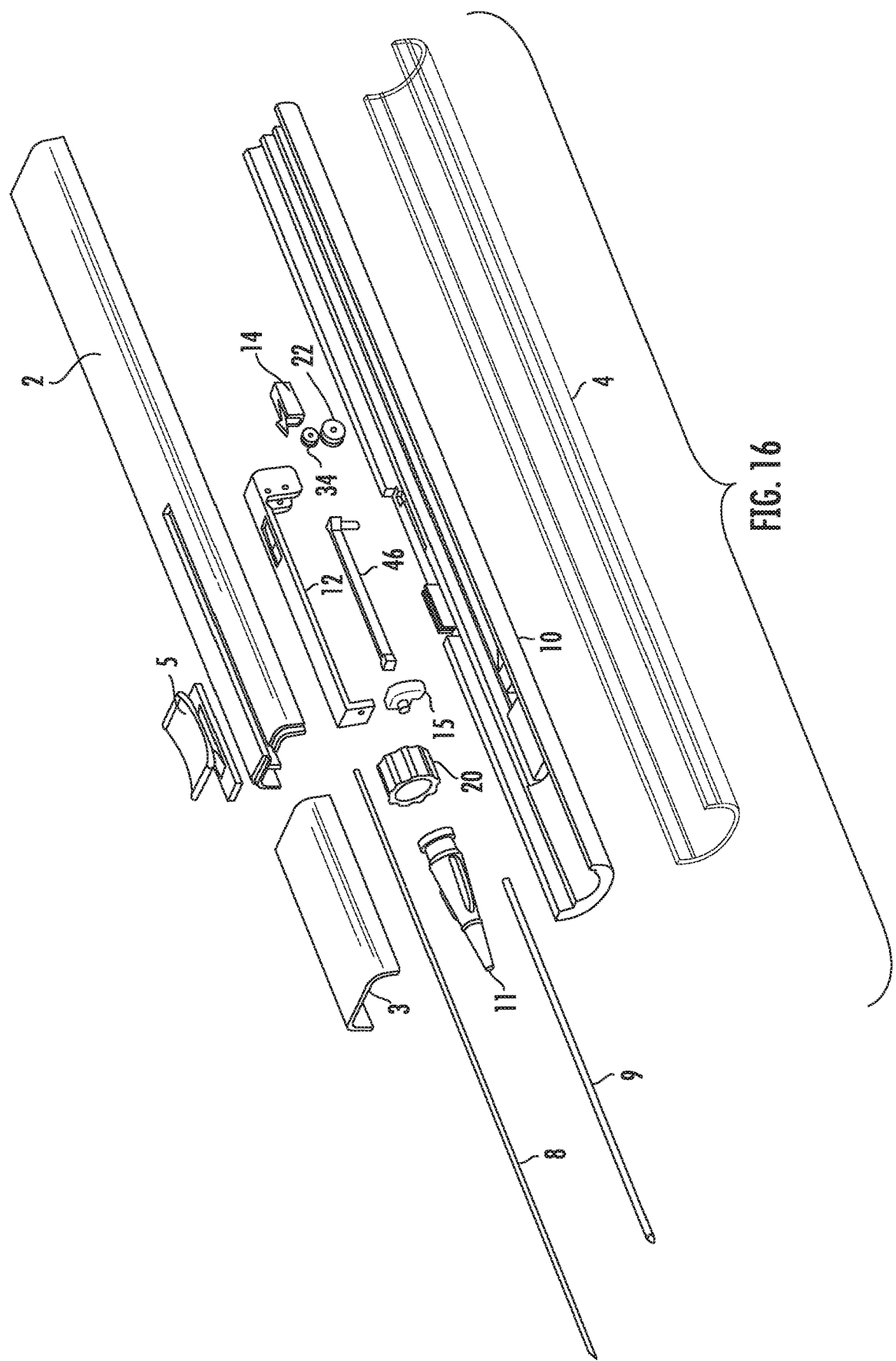
FIG. 16 is an exploded, perspective view of the individual components.

Between the retraction frame struts 31 and 32 is a pulley system for retraction of the guidewire. The pulley system comprises the upper tension pulley 34 and the retraction pulley 22 which travels in a track 43 in the lower rail insert 10. See FIGS. 12,16 and 17. However, it is within the scope of the invention to reverse the orientation of the tension and drive pulleys or have additional pulleys. The circumferential surfaces of the pulleys are in contact with each other, and these surfaces contain central grooves 38 and 39 that form a channel for receipt of the guidewire 7. The channel defines an aperture 41 shown in FIG. 12. A spur gear 33 is in substantially rigid communication with the drive pulley 22. The teeth of the spur gear 33 are configured to cooperate with the teeth of a longitudinally oriented elevated rack 37 on the lower rail insert 10 for relative movement therebetween. As the finger slide 5 is manually retracted in the proximal direction by the user, the retraction frame 12 slides proximally along the lower rail insert in a substantially 1:1 ratio. However, the guidewire 7 begins to retract at a predetermined ratio faster than the retraction frame 12, that is, greater than 1:1. The spur gear 33 contacts the elevated rack 37, causing the spur gear 33 to rotate, thus rotating the retraction pulley 22 to which it is fixedly attached. In this portion of lower rail insert 10, the retraction pulley 22 is constrained, but freely rotatable with the confines of track 43 and, as shown, does not substantially contact the lower portion of track 43. Thus, the retraction pulley 22 rotates at a faster rate than would be seen if rolling on the surface of the track 43.

In conjunction with the tension pulley 34, the retraction pulley 22 retracts the guidewire 7 into the protective housing 1. See FIGS. 13, 14 and 15, for example. The pulleys 34 and 22 are supported by the retraction frame struts 54 and rotate about connections 35. The ratio of the diameter of the spur gear 33 to the retraction pulley 22 dictates the rate at which the guidewire 7 is retracted, as this gear ratio will cause a greater length of guidewire 7 to be retracted for each unit length of motion of the finger slide 5. For example, a 1 cm proximal movement of the finger slide 5 may lead to 2 cm, or greater, length of guidewire 7 to be retracted into the housing 1. This feature allows more rapid retraction of the contaminated guidewire 7 as well as better ergonomics for a single hand-operated device. It is also within the scope of the present invention to consider any potential arrangement or number of gears, pulleys, or gear teeth, etc., to perform the function of guiding or advancing/retracting the wire.

Figure 22:
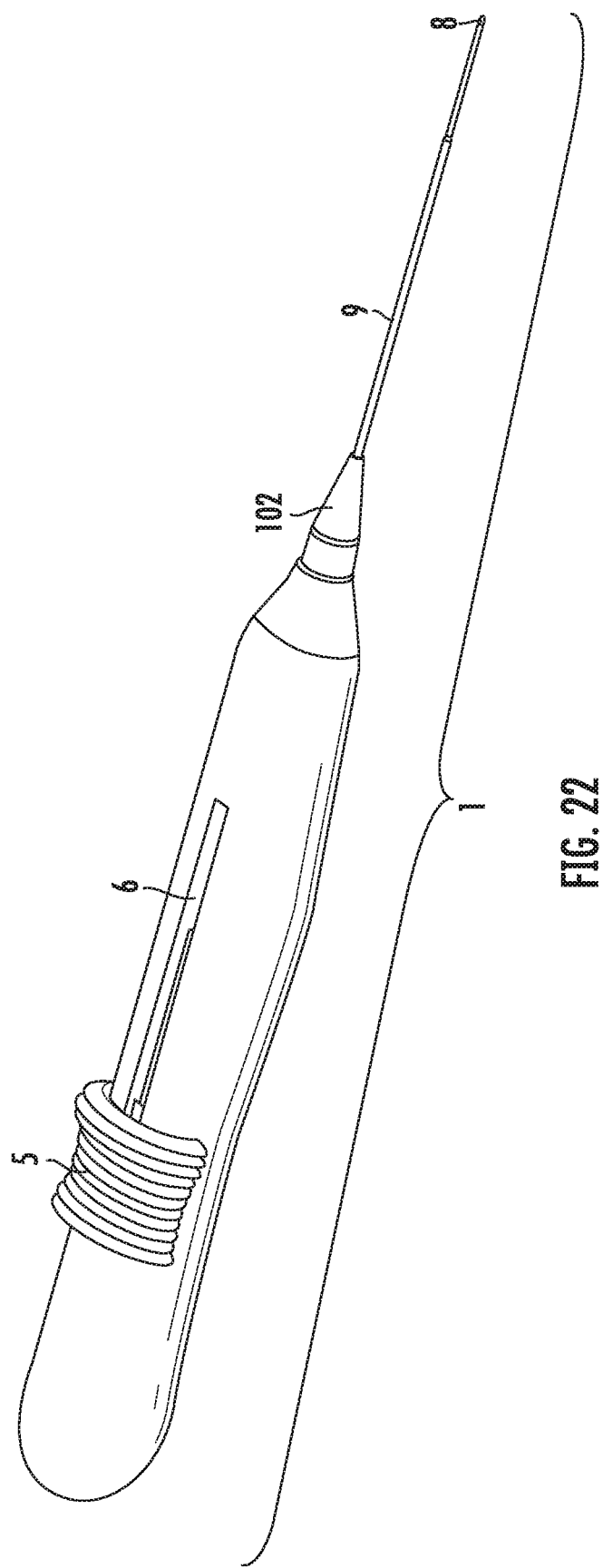
FIG. 22 is a perspective view of a vascular access catheter containing needle safety device in the starting position.

As shown in FIGS. 22 and 23, the distal portion of the integrated device has a break away cone 102. Additionally, positioned just distal to the distal end plate of retraction frame 12 is a disc shaped cap 100. The catheter hub 11 is fixedly attached to the catheter 9. The disc shaped cap 100 is interposed between the catheter hub 11 and the advancement frame 12. As the retraction frame 12 urges the catheter hub 11 forward, the interposed cap 100 also slidably advances over the needle 8. After the hub 11 and the cone 102 merge and become attached, the cap 100 continues to advance a short distance. The cap 100 then irreversibly snaps into a cap groove 101 in the distal opening of the housing. This provides a near complete enclosure for housing the needle and guidewire once in the fully retracted position as shown in FIG. 23. This cap 100 prevents a finger or other body part from coming in contact with the needle tip once it has been retracted. Furthermore, the cap 100 provides enclosure of the needle 8 and wire 7 such that trace blood products are contained within the housing 2. Both sharp injury and blood surface contamination are minimized with this aspect.

Retraction of the needle 8 will now be elucidated. The frame 12 contains an upper, longitudinal body 52. A needle retainer hook 16 (FIG. 8) is positioned on a proximal portion of the retraction frame body 52. When the device is fully deployed in its most advanced or distal position, the needle retainer hook 16, irreversibly engages the needle retainer 15. The retainer hook 16 as shown defines a flexible tab, so as to slide over the needle retainer 15, wherein the retainer hook 16 then contacts and securely connects with the needle retainer 15. Audible or tactile feedback may be appreciated by the user when this occurs. Thereafter, any proximal movement of the finger slide 5, and coupled retraction frame 12, will also lead to retraction of the needle 8 into the protective housing 1.

Figure 5:
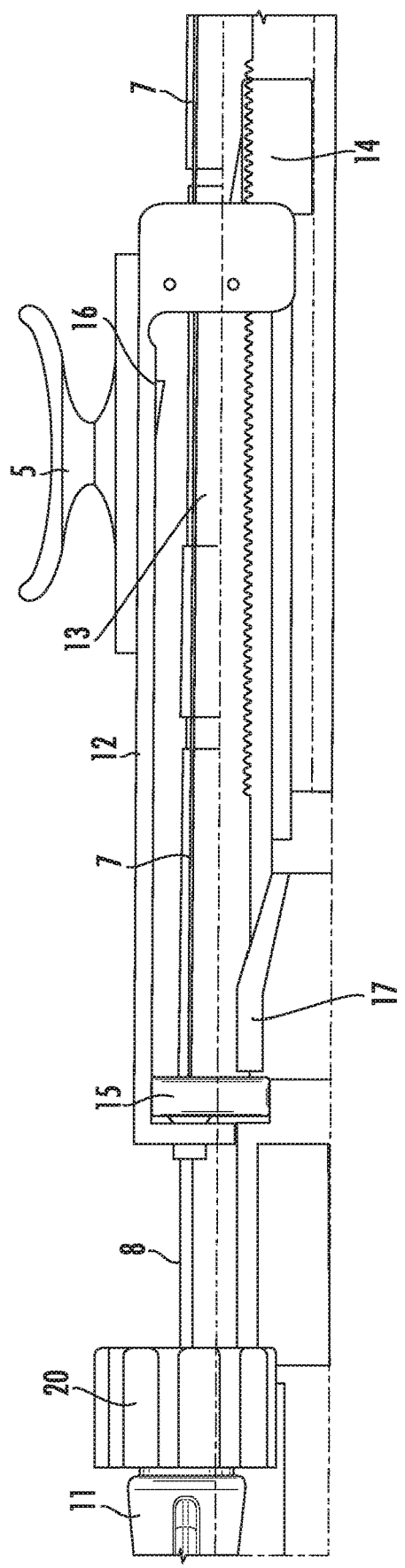
FIG. 5 is a side elevational, partially broken away, view of the needle retraction frame and needle/catheter assembly in the starting position prior to catheter deployment.
Figure 6:
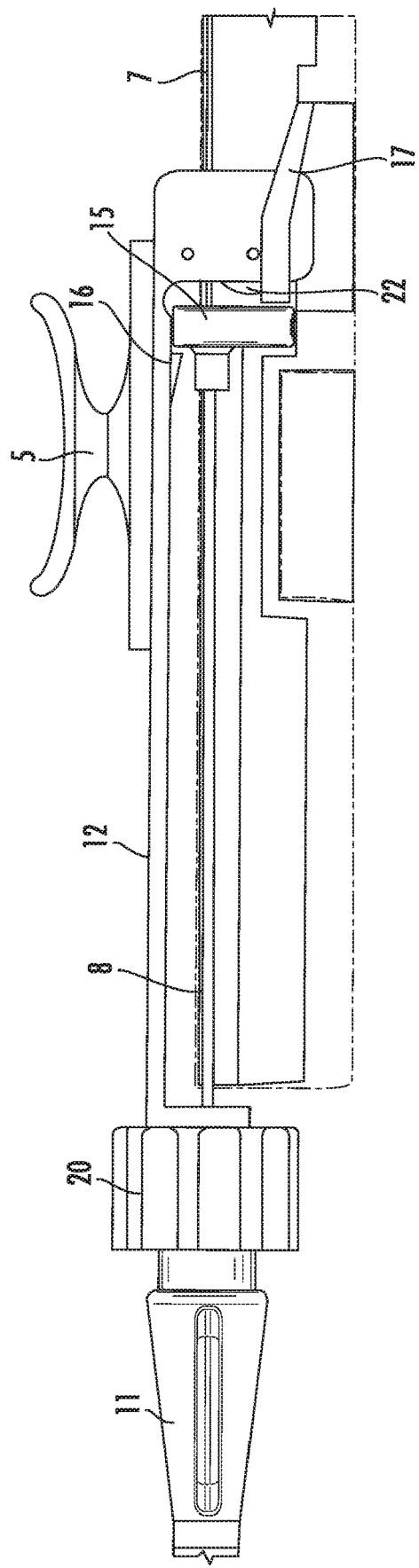
FIG. 6 is a side elevational, partially broken away, view of the needle retraction frame and needle/catheter assembly in the fully advanced position, just prior to retraction.
Figure 7:
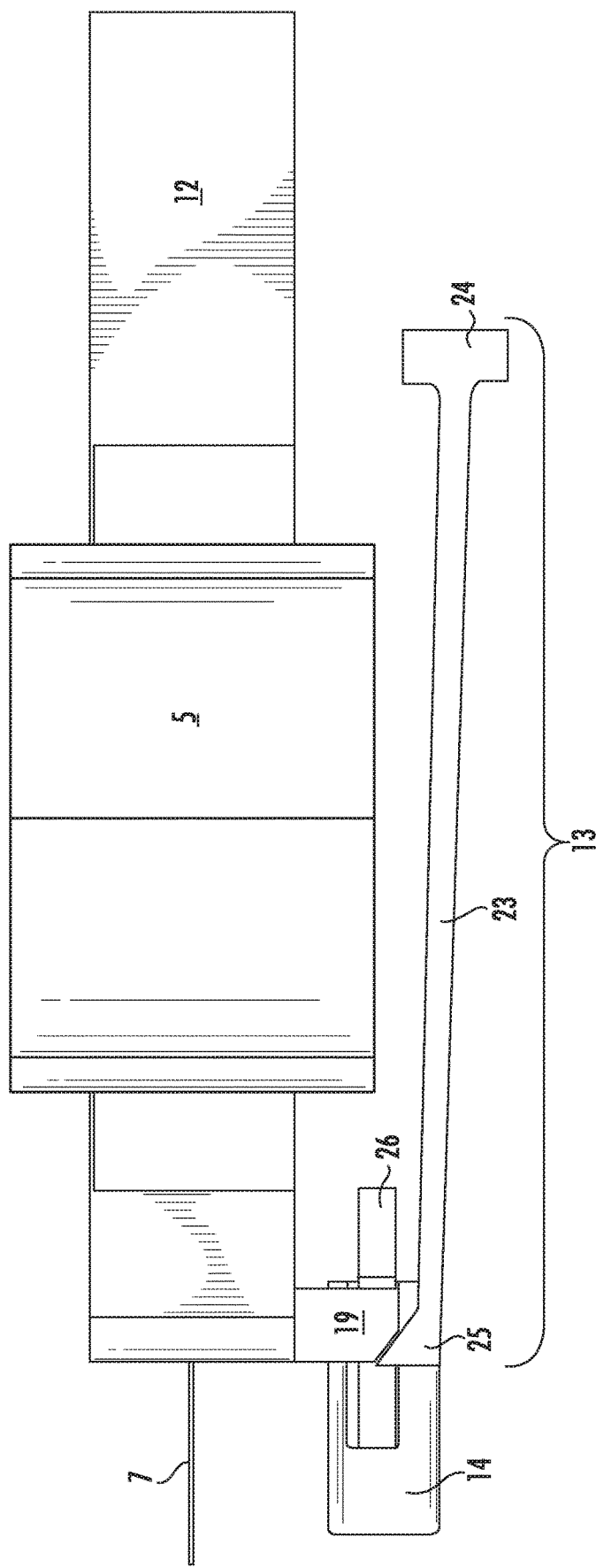
FIG. 7 is a top plan, enlarged view of a portion of the spring-loaded safety mechanism.

According to one aspect, additional mechanisms are provided to secure the needle 8 to the retraction system for containment. A flexible needle retainer clasp 17, shown in FIGS. 5 and 6, is provided within the distal lower rail insert 10. This needle retainer clasp 17 holds the needle retainer 15 in the starting position for use during the catheter access procedure as shown in FIG. 5. Once the catheter is deployed and the retraction frame 12 is advanced into the most distal position, the drive pulley 22 depresses the flexible, tab-like needle retainer clasp 17, disengaging the needle retainer 15 from the lower rail insert. This in turn allows the needle 8 to be retracted into the safety housing 1 by the needle retainer hook 16 on the retraction frame 12 as shown in FIG. 6.

As thus described, the active portion of needle and guidewire retraction involves the user actively actuating the finger slide 5 proximally to retract the needle 8 and guidewire 7. According to another aspect, shown in FIG. 9, when the finger slide 5 reaches the most proximal portion of the longitudinal housing slot 6, a passive, spring loaded retraction mechanism is engaged causing rapid and substantially complete retraction of the needle 8 and guidewire 7 into the protective housing 1. The passive component of this two-system (active and passive) mechanism for the safe retraction of contaminated needle and guidewire, will now be described.

The passive safety system described herein and shown in FIGS. 8, 9, 10, and 18-21, generally comprises a safety trigger 13, a safety shuttle 14, and a compression spring 28. Further, the safety trigger 13 is generally elongate and comprises a distal transverse member 24, a central longitudinal member 23, and a proximal trigger latch 25, of which form and functions will be described in detail. The trigger 13 is disposed within the housing 1 and along the lateral aspect of the lower rail insert 10 in a trigger housing 51.

Figure 17:
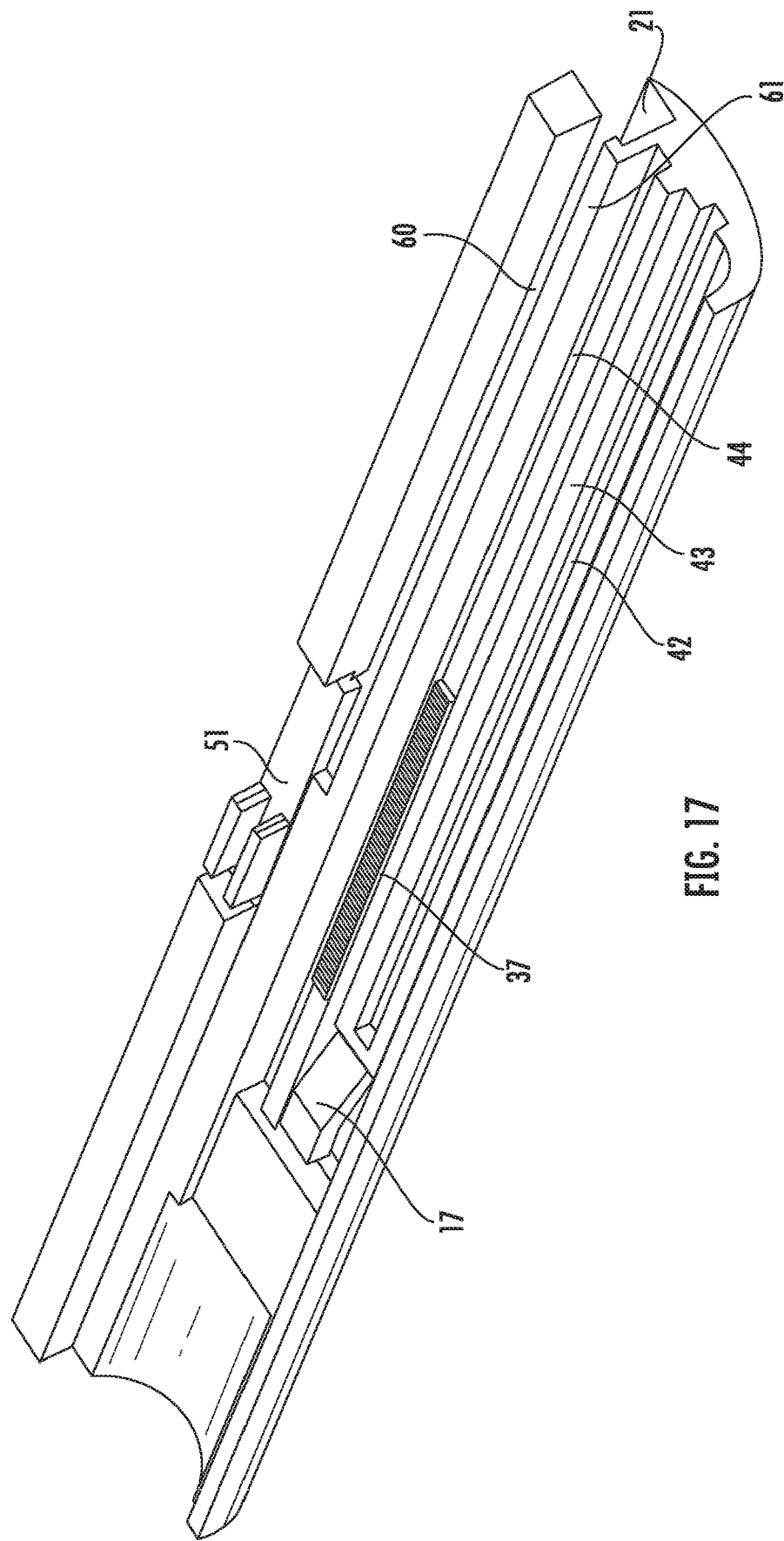
FIG. 17 is a perspective view of the lower rail insert.

A channel in the form of a safety shuttle conduit 21 is defined by the housing 1 and portions of the lower rail insert 10 as shown in FIGS. 12 and 17. Slidably disposed within the safety shuttle conduit 21 is the compression spring 28 and safety shuttle 14. The safety shuttle (FIG. 10) 14 comprises an upper shuttle tab 26 with carrier hook 70, an outer body 27, and a spring post 29 for receipt of the proximal end of the compression spring 28.

Figure 9:
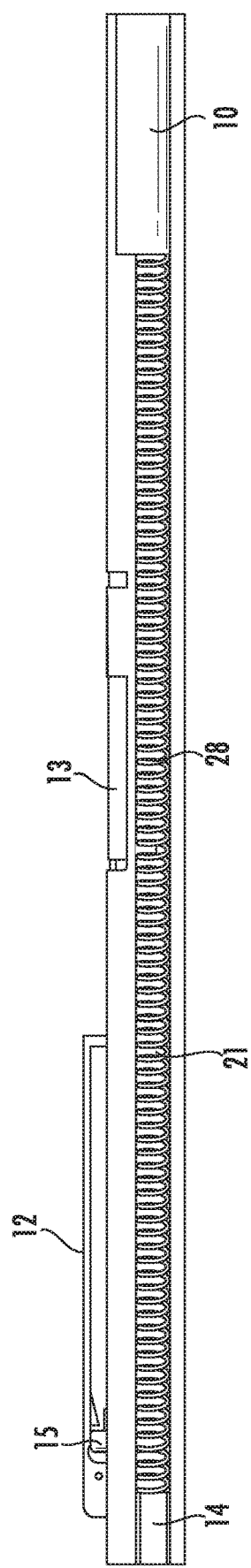
FIG. 9 is a cross-sectional view, partially broken away, of the needle safety device in the fully retracted position showing the deployed spring mechanism.
Figure 10:
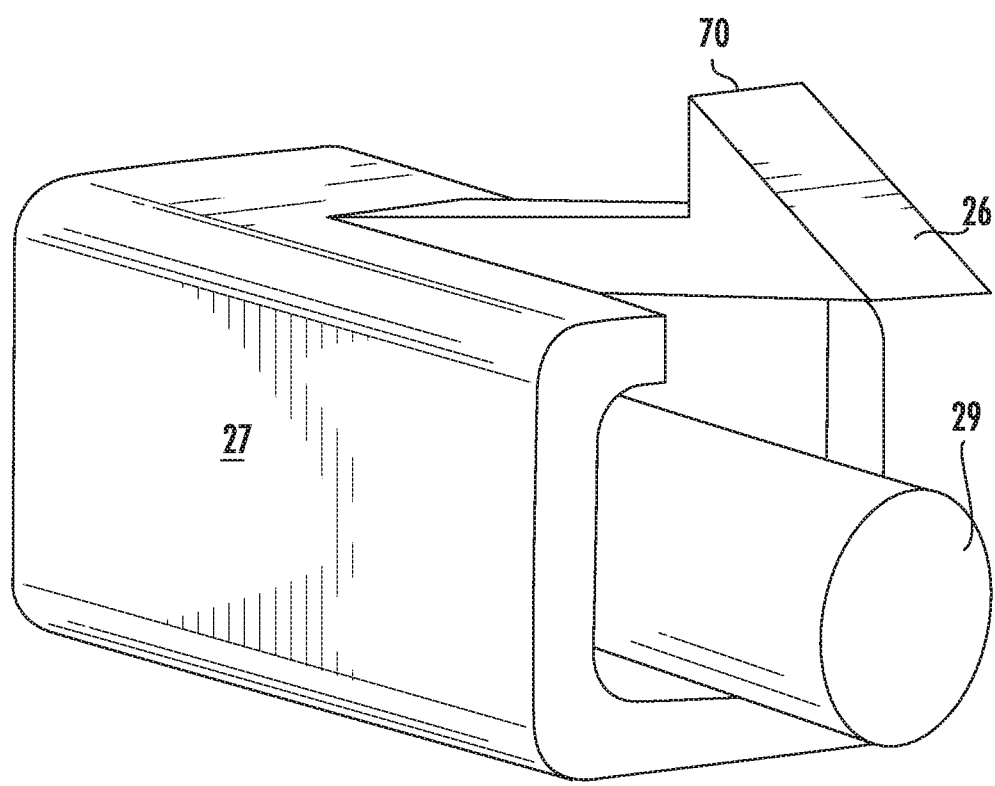
FIG. 10 is an enlarged, perspective view of the safety shuttle.

After the catheter 9 has achieved vascular placement, retraction of the needle 8 and substantial lengths, in many instances, of the guidewire 7 begins. For purposes of this disclosure, the initial, or starting, position for the safety device according to the present invention is the position where the needle 8 and guidewire 7 are to be rapidly and effectively withdrawn. This initial position is shown in FIGS. 2 and 9, for example. Retraction is initiated by proximal movement of the tab or slide 5 along the upper surface of the housing 1. This proximally moves the retraction frame 12. As described above, the distal end surface of the retraction frame 1 contacts the needle retainer 15 thereby proximally moving it and retracting the needle 8. This same movement of the retraction frame 12 also rotates the retraction pulley 22 which is supported by the retraction frame 12 as the retraction pulley traverses the length of rack 16 on the lower rail insert 10. For the safety device including the active and passive retraction systems, the length of the rack 16 may be modified. Although FIG. 2 shows the rack 16 extending a predetermined distance, the device utilizing both active and passive retraction systems may include a longer rack 16 (not shown), extending closer to the proximal end of the lower housing 14. As such, the translation forces initially applied to the tab 5 retract the needle 8 and the guidewire 7 wherein the guidewire, having a greater length than the needle 7, is also retracted, but at a greater rate due to the pulley system. The safety shuttle 14, at this stage, does not move proximally with the retraction frame 12. This is because with the safety shuttle is retained in position the safety trigger as shown if FIGS. 13, 18 and 19. A vertical component of the proximal trigger latch 25 engages the shuttle retainer tab 61 defined by the safety shuttle 14. The safety trigger is supported by a channel defined by the lower rail insert 10. This position maintains the spring 28 compressed in the starting position as shown in FIG. 2. If the safety shuttle 14 were unrestrained, forces applied by the spring 28, under predetermined compression, would otherwise urge the safety shuttle 14 in the proximal direction.

Figure 3:
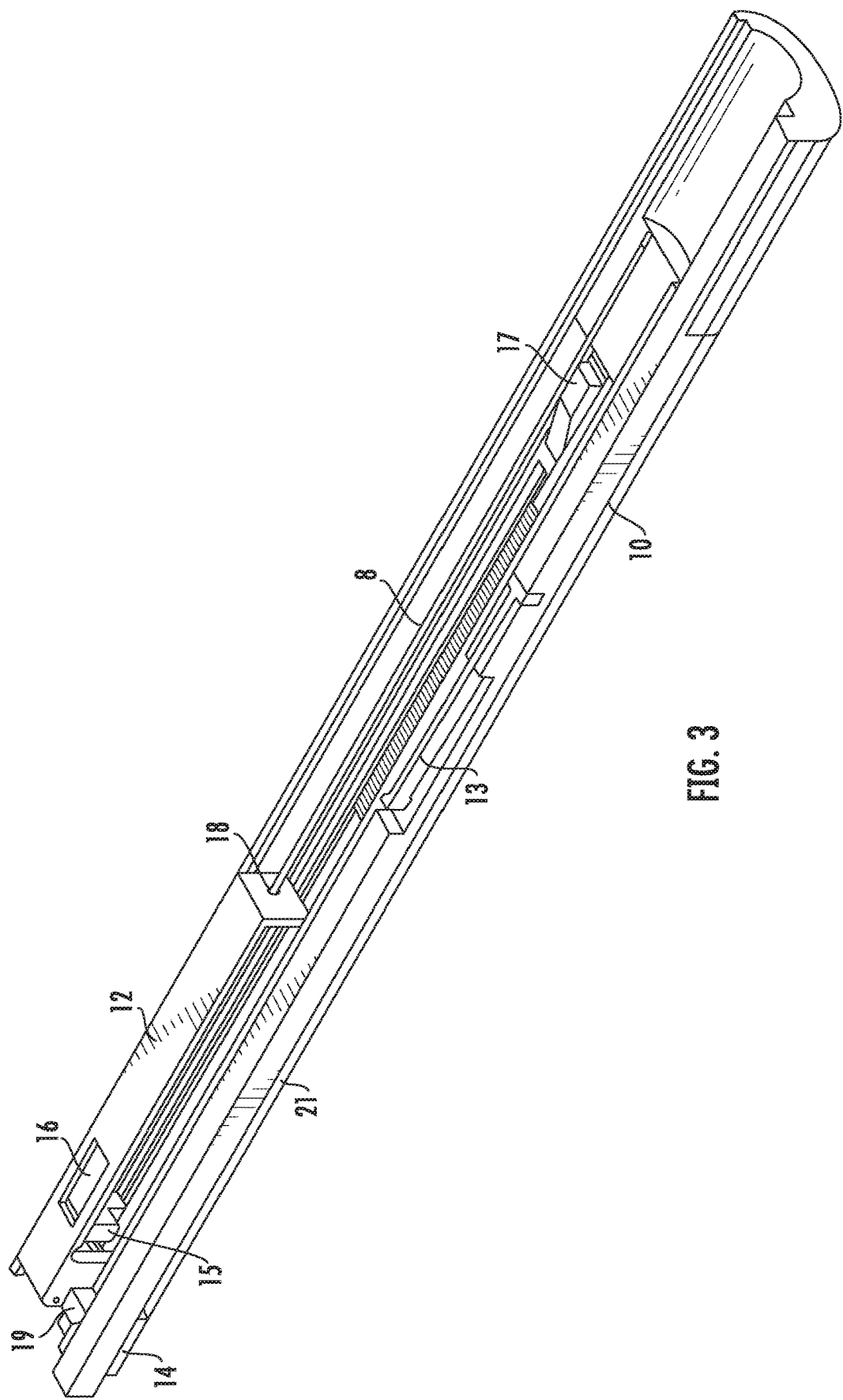
FIG. 3 is a perspective, partially broken away view of the lower housing and frame of the needle safety device in the fully retracted position.
Figure 4:
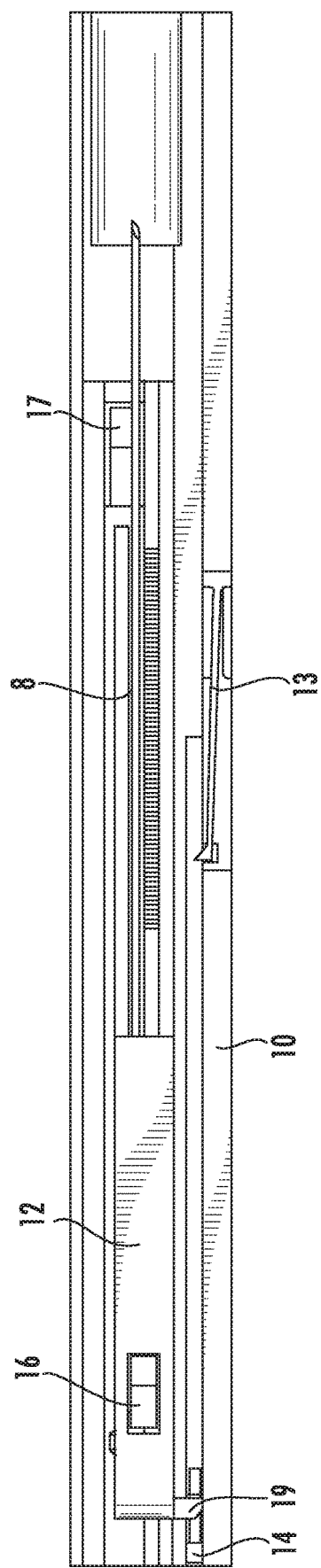
FIG. 4 is a top plan view of the broken away image of FIG. 3 in the fully retracted position.
Figure 18:
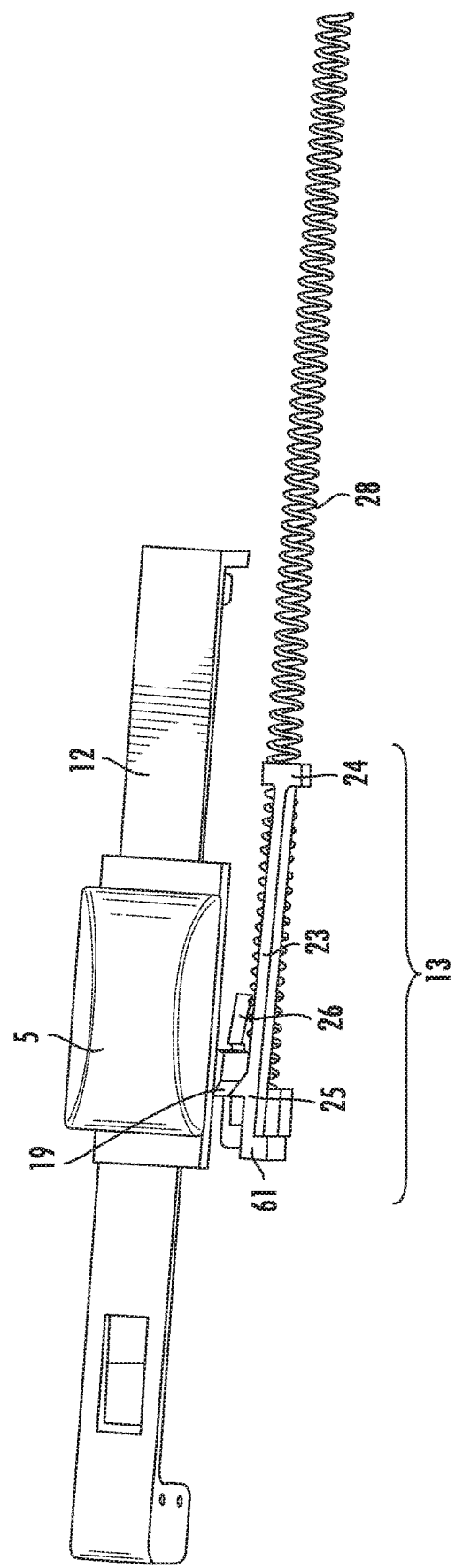
FIG. 18 is a perspective view of the safety device.
Figure 19:
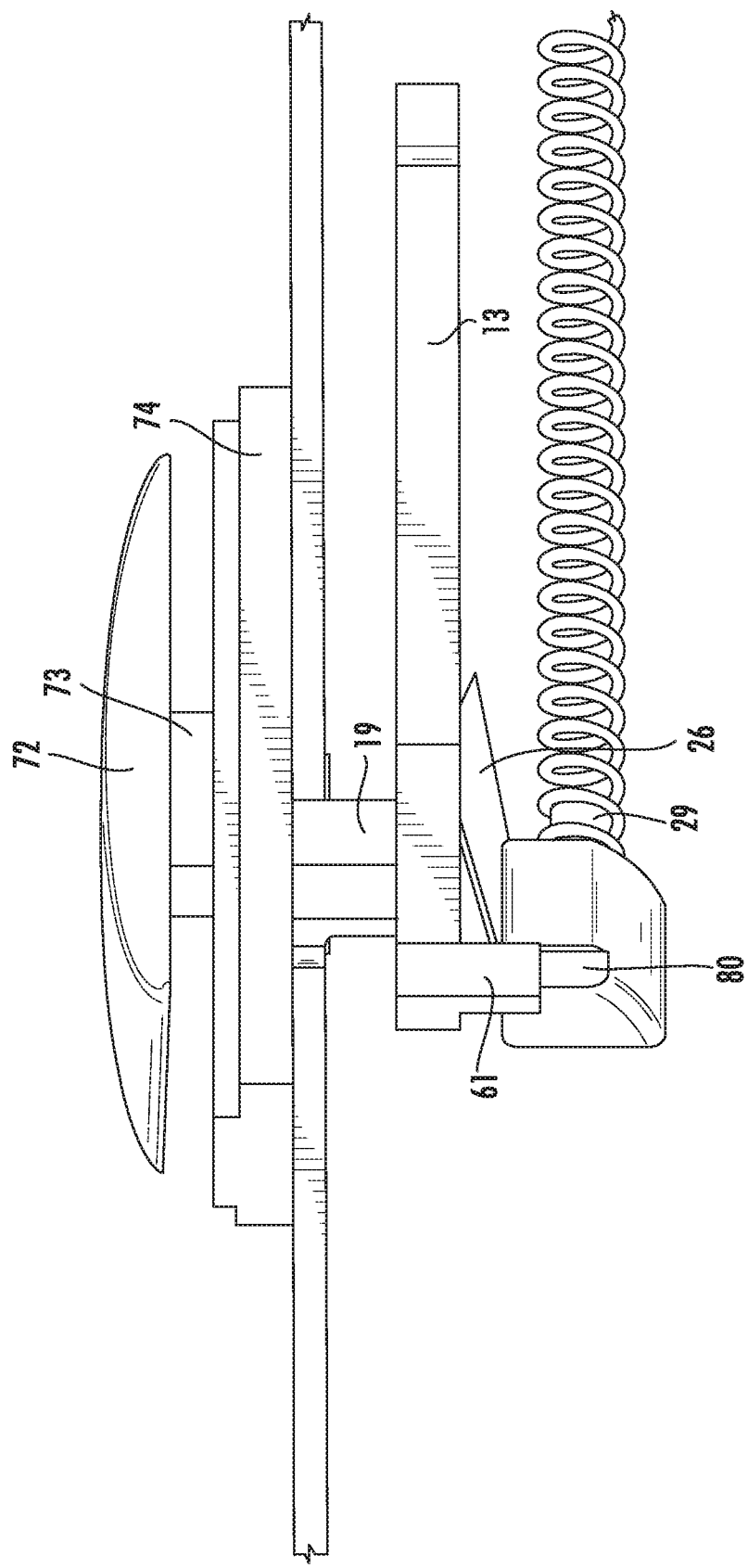
FIG. 19 is an enlarged, perspective view of the safety system.
Figure 20:
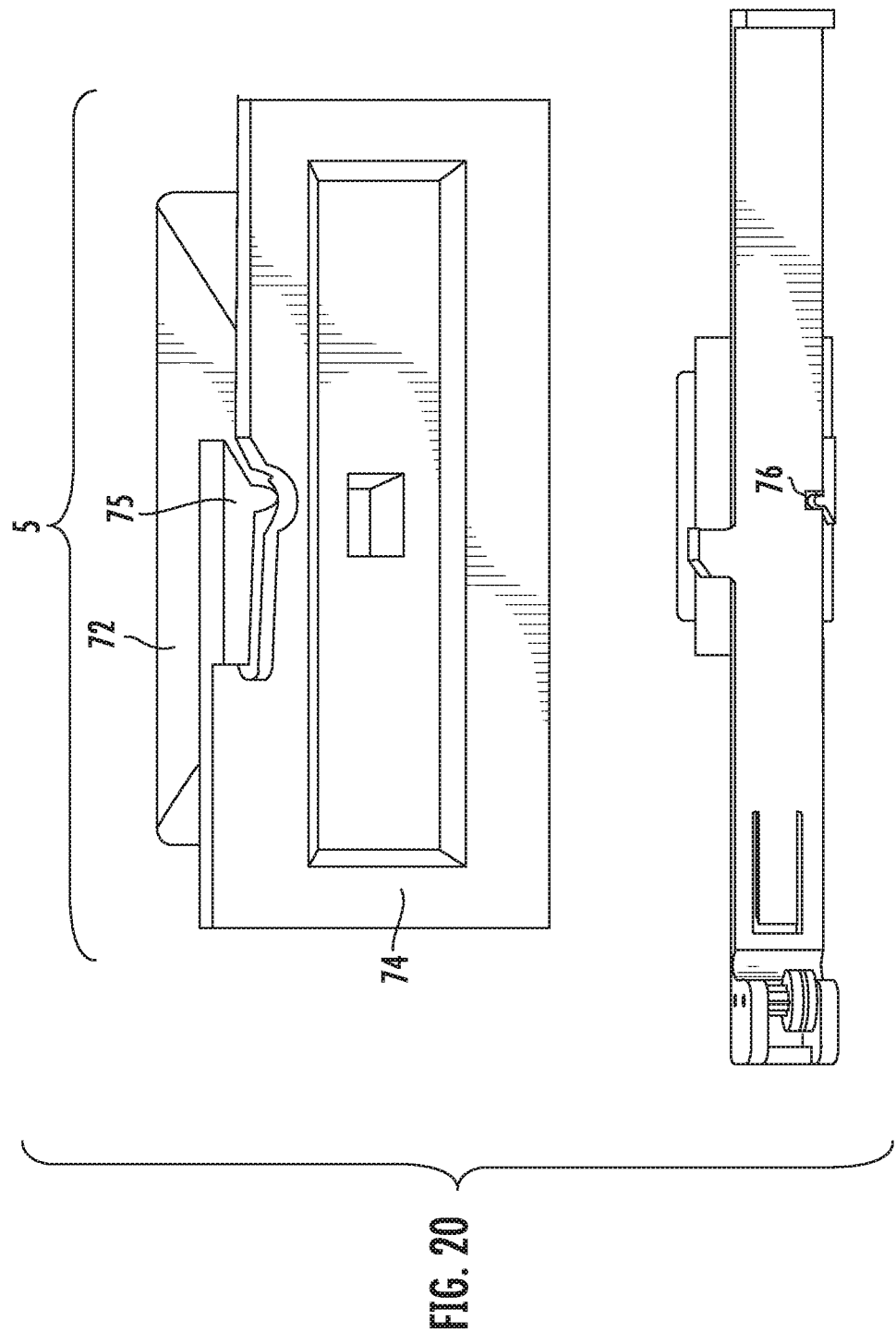
FIG. 20 illustrates enlarged perspective views of components of the safety system, showing the relationship of the finger slide and the retraction frame.

After initial retraction of at least a portion of the needle 8 and guidewire 7, it is necessary to complete retraction. And the guidewire 7 length is sufficiently greater than the needle, so fast and controlled retraction of the guidewire is necessary to avoid the aforementioned safety concerns. Therefore, it is desirable to release the safety shuttle 14 from the safety trigger 13 to enable spring 12 forces to rapidly retract any remaining needle 8 length and/or guidewire length 7, as shown in FIGS. 3, 18 and 19. The retraction frame 12 includes a side tab 19 extending outwardly form the proximal end surface of the retraction frame 12 and is positioned to cooperate with and to disengage the safety trigger 13 while also preventing distal movement of the retraction frame. As the finger slide 5 and the retraction frame 12 reach the position wherein the tab 5 has reached the proximal end of the upper housing slot 6, the retraction frame side tab 19, slidably engages the hook-like portion 70 of the shuttle tab 26 extending from the safety shuttle 13. The shuttle tab 26 is semi-rigid and allows the side tab 19 to slidably course over the superior aspect of the downward flexing shuttle tab 26 until the hook-like portion 70 of the shuttle tab 26 engages, preferably irreversibly, with the distal face of the side tab 19. At this position, distal movement of the retraction frame 12 is hindered by the shuttle tab 26.

Minimal additional proximal movement of the finger slide 5 and the retraction frame 12 results in the retraction frame slide tab 19 contacting, and laterally displacing, the trigger latch 25 of the safety trigger. The majority of the trigger 13, is held in place by the trigger housing 51, but the proximal aspect of the trigger 13 is flexible. When the trigger 13 flexes laterally by the pressure imposed by the retraction frame side tab 19 on the trigger latch 25, the shuttle retainer tab 61 disengages from a retainer tab recess 80 in the safety shuttle 14. As such, the safety shuttle 14, under compression forces of the spring, is free from constraint so as be forced proximally, thereby also forcing the retraction frame 12 therewith. The only constraint on the system at this point is the tab 5 within the upper housing longitudinal slot 6. This, restraint therefore, is removed.

Figure 21:
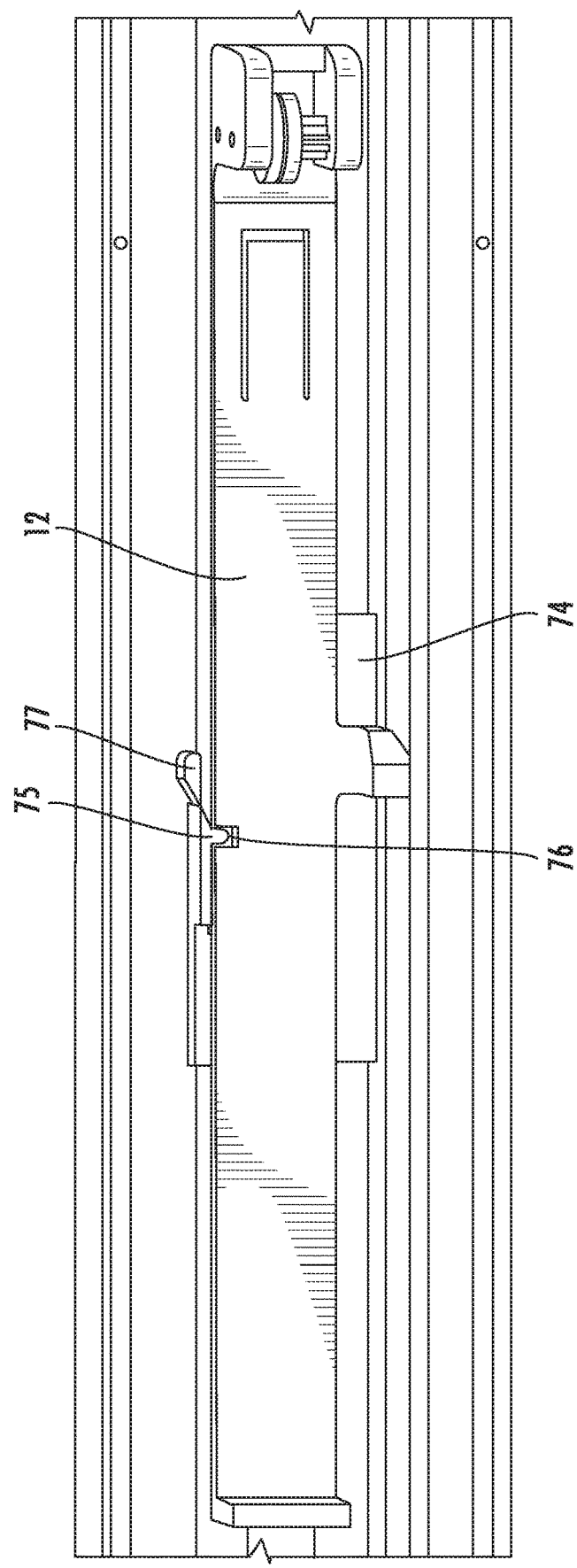
FIG. 21 is an enlarged perspective view illustrating the slide clip stripper post.

At this point, movement of the retraction frame 12, carrying the needle 8 and guidewire 7, is prevented from traveling proximally with the safety shuttle 14 by a breakaway connection between the finger slide 5 and retraction frame 12 herein described. The finger slide 5, is detachably connected to the components described, but cannot travel proximally beyond the confines of the longitudinal housing slot 6. The finger slide 5, shown in FIG. 20, comprises a finger tab 72, slide neck 73 (shown in FIG. 19), slide plate 74, and a slide clip 75. The slide clip 75 is flexible and extends from the slide plate 74, and is in connection with a retraction frame notch 76. As shown in FIG. 21, a slide clip stripper post 77 is located in the internal surface of the proximal upper housing 2, and with minimal final proximal movement of the finger slide 5, the fixed slide clip stripper post 77 unclips and strips away the slide clip 75.

In the passive retraction phase, utilizing the passive retraction system, all components are unrestrained from internal components of the safety device. The compression spring forcefully extends in the proximal direction, carrying with it the safety shuttle 14, retraction frame 12 (thereby rotating the retraction pulley 22 as it traverses the length of the rack 16 which is appropriately sized for the passive retraction), needle retainer 15 and needle 8, and guidewire 7, thus completing the safety mechanism. This rapid proximal motion causes rapid retraction of the guidewire 7 which has initially been retracted a predetermined amount. Thus, a short length of guidewire is rapidly retracted by the passive retraction system in a controlled manner. While not being bound by any theory, this is advantageous as rapid retraction of a typically very long guidewire 7 would be uncontrolled (e.g. "spaghetti noodle" effect) and unsafe from a clinical standpoint. Although this passive safety mechanism is forceful and rapid, the devices are retracted in a controlled manner as guided by various channels, grooves, and conduits within the lower rail insert 10. Specifically, the safety shuttle 14 has a generally curvilinear shape, and travels in a safety shuttle conduit 21, of similar shape, and formed by the portions of the lower rail insert 10 and internal lateral wall of the lower housing 14. See FIG. 17. The shuttle tab 26 of the safety shuttle 14 extends slightly more above the shuttle body, and thus must be allowed to travel proximally, but not in the confines of the safety shuttle conduit 21. Therefore, the lower rail insert comprises a safety shuttle groove 60, openly disposed along the upper surface of the safety shuttle conduit 21. Furthermore, the retraction frame side tab 19 must be allowed to travel and carry the components of the retraction frame 12 as it is newly attached to the safety shuttle 14 system. A frame tab riser 81 is disposed just central to the safety shuttle groove 60. This frame tab riser 81 provides a surface over which the retraction frame side tab 19 may controllably travel.

Figure 13:
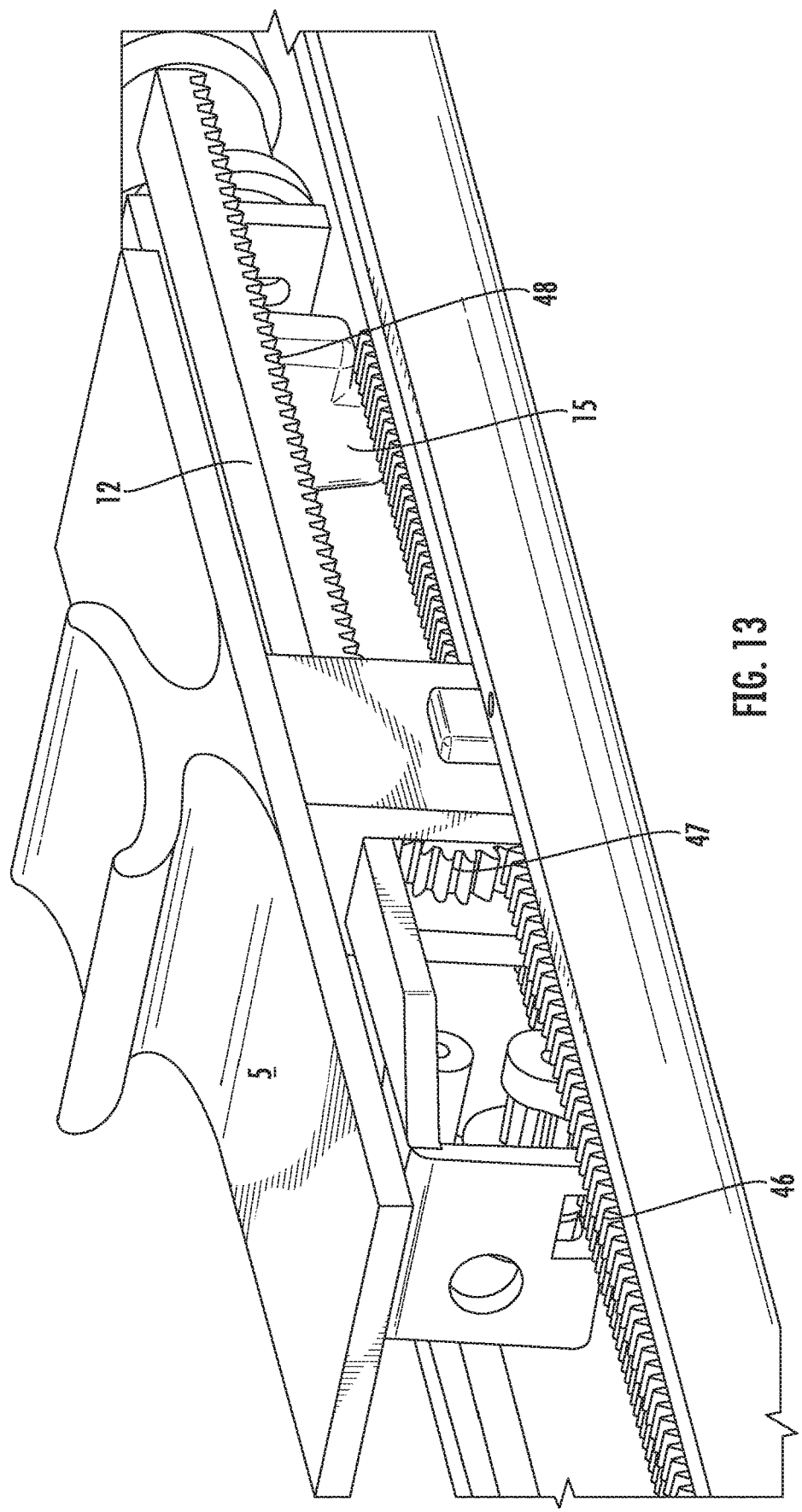
FIG. 13 is an enlarged, partially broken away, perspective view according to alternative aspect.
Figure 14:
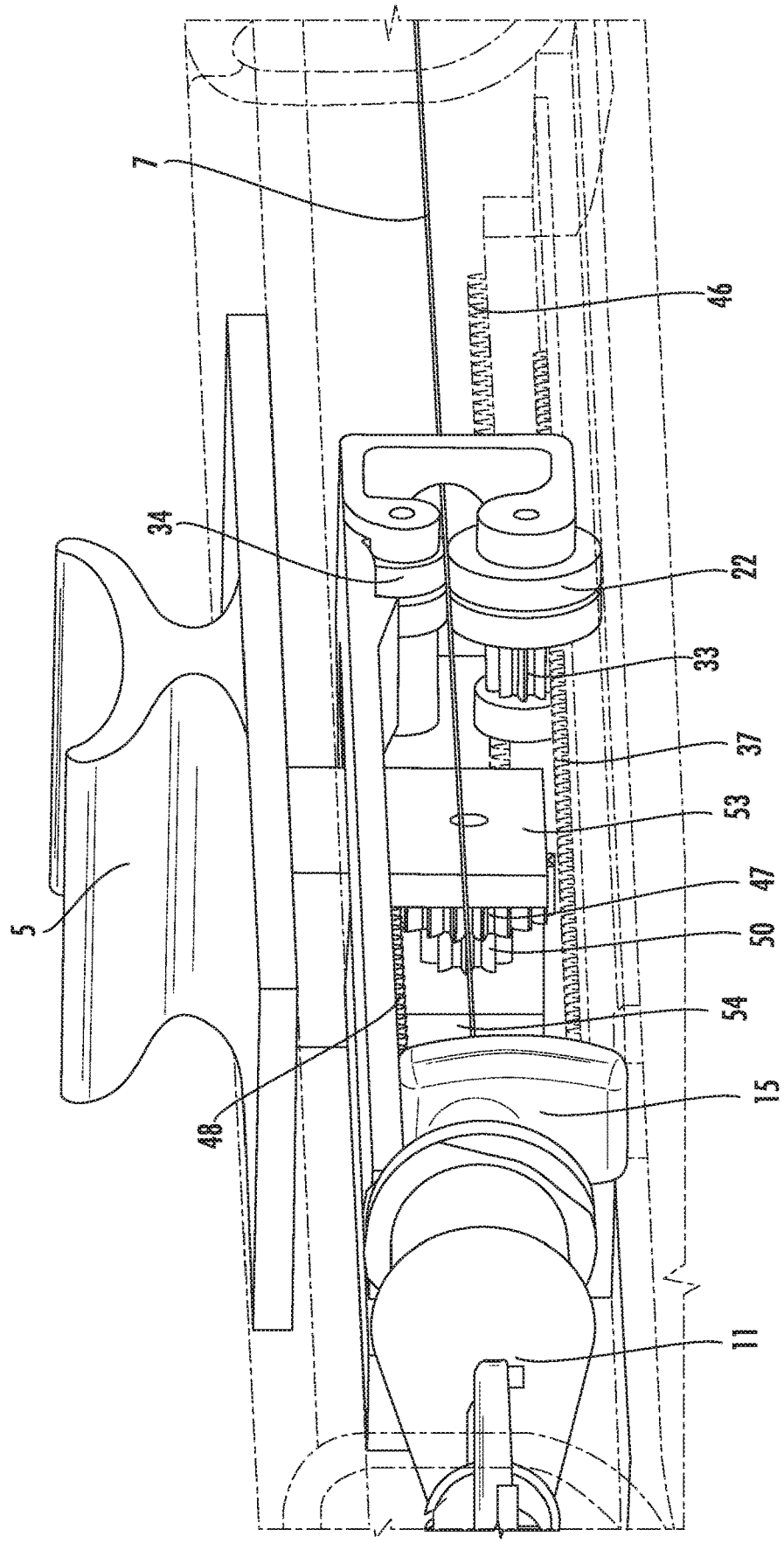
FIG. 14 is an enlarged, partially broken away, perspective view of FIG. 13 showing the retraction frame, the pulley system, and longitudinal rack of the lower rail insert.
Figure 15:
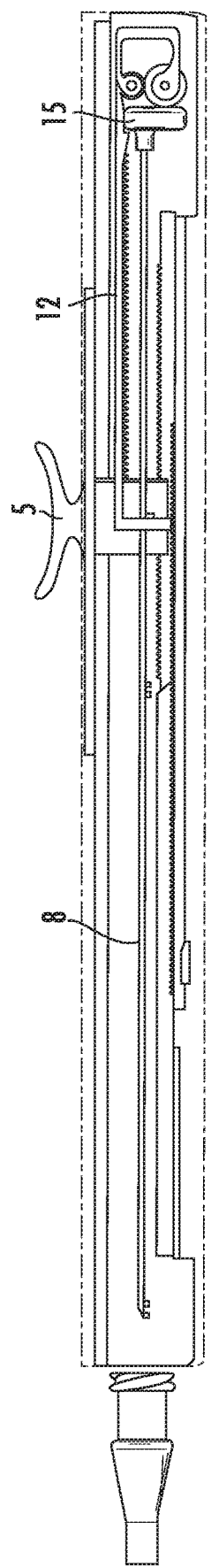
FIG. 15 is a side, partially broken away view of FIG. 13 in the retracted position.

An alternative aspect of the safety device disclosed herein relies on a single phase of continuous active retraction of the needle 8 and guidewire 7. In this alternative aspect a second pulley system is provided for additional rapid retraction of the guidewire 7 and/or needle 8. As shown in FIGS. 13-14, the lower surface of the retraction frame body 12 contains a rack 48. A second spur gear 47, aligned with an upper second rack 48, is held in place with struts 54 in rigid communication with the finger slide 5. This larger spur gear 47 is in rigid communication with a smaller spur gear 50. Smaller spur gear 50 is thus in line with a longitudinally extending raised third rack 46 that extends along the lower rail insert 10. Once the finger slide tab 5 and the retraction frame 12 are pulled proximally by the user, spur gear 50 is rotated by communication with rack 46 due to cooperating surface configurations, i.e., surfaces defining corresponding teeth. This in turn rotates first spur gear 47 which communicates with rack 48 on the retraction frame 12. The rotation of first spur gear 47 retracts the frame 12 rapidly into the protective housing 1. The ratio of diameter of spur gear 47 to second spur gear 50 dictates the rate at which the retraction frame moves proximally. This proximal movement of the retraction frame 12 leads to retraction of the needle 8 and guidewire 7 as detailed above.

While exemplary embodiments have been shown and described above for the purpose of disclosure, modifications to the disclosed embodiments may occur to those skilled in the art. The disclosure, therefore, is not limited to the above precise embodiments and that changes may be made without departing from its spirit and scope.

What is claimed is:

1. A medical assembly safety device for two-stage retraction of a needle and a guidewire after endovascular catheter placement wherein the catheter remains positioned and the needle and guidewire are to be retracted within the safety device comprising:
    a housing extending longitudinally between proximal and distal ends and having an upper housing and defining a cavity extending along at least a portion of the longitudinal length of the housing, said housing being configured for receipt of the retracted needle and guidewire;
    a needle retraction assembly within said housing comprising a retraction frame, a lower frame member upon which said retraction frame slidably moves, and a tab coupled to said retraction frame and extending from said housing cavity and exterior to said upper housing wherein said needle retraction assembly retracts the needle and is configured to retain the needle after retraction and wherein said external tab is moveable a predetermined distance along said housing and proximal movement of said external tab moves said retraction frame proximally to retract the needle at a first retraction rate;
    a guidewire retraction assembly within said housing for retracting the guidewire, said guidewire retraction assembly comprising a pulley system operatively connect to said retraction frame, said pulley assembly including a retraction pulley configured to cooperate with said lower frame member and a tension pulley for retracting the guidewire at a second retraction rate wherein said second retraction rate is greater than said first retraction rate wherein an active retraction system utilizes said needle retraction assembly and said guidewire retraction assembly for actively retracting the needle and guidewire; and
    a passive retraction system within said housing and comprising a safety shuttle and a compression spring operatively connected to said safety shuttle wherein said safety shuttle is restrained when said active retraction system is operative and wherein said safety shuttle is released by proximal movement of said retraction frame and passive retraction system utilizes said pulley system to rapidly and passively retract remaining lengths of the guidewire within said housing wherein said guidewire is retracted a third retraction rate by said passive retraction system wherein said third retraction rate is greater than said second retraction rate.

2. The medical assembly safety device according to claim 1 wherein said retraction pulley and tension pulley each comprise an adjacent outer surface define a channel for receipt of the guidewire.

3. The medical assembly safety device according to claim 2 wherein said retraction and tension pulleys are rotatably mounted to a strut extending from said retraction frame.

4. The medical assembly safety device according to claim 3 wherein said device further comprises a lower rail insert positioned within said cavity on said lower housing, and a rack positioned along a length of said lower rail insert, said rack having an upper surface with a first surface configuration, said rail insert being positioned so as to cooperate with said retraction pulley.

5. The medical assembly safety device according to claim 4 wherein said retraction pulley includes an outer surface having a second configuration for cooperating with said rack first surface configuration to rotate said retraction pulley on said frame strut when forces are applied to the guidewire retraction assembly.

6. The medical assembly safety device according to claim 5 wherein said retraction pulley includes a spur gear extending outwardly therefrom and defining said second configuration for cooperating with said rack wherein said rack first configuration and said spur gear second configuration are mating teeth and movement of said retraction frame proximally moves said retraction pulley along the length of said rack so as to rotate said retraction pulley and said tension pulley in opposite directions so as to retract the guidewire.

7. The medical assembly safety device according to claim 1 wherein said external tab extends through an aperture defined by said upper housing and is defined by a slide which extends from below said upper housing and through said upper housing aperture.

8. The medical assembly safety device according to claim 1 wherein said housing comprises a lower housing for cooperating with said upper housing and defining said housing cavity and a lower rail insert positioned within said housing cavity and extending along an upper surface of said lower housing and said passive retraction system is positioned in a second cavity defined by said lower rail insert and said housing.

9. The medical assembly safety device according to claim 8 wherein said passive retraction system compression spring and said safety shuttle are positioned within said second cavity wherein said safety shuttle is operatively connected to said retraction frame, and a safety trigger for selectively restraining said safety shuttle relative to said retraction frame and wherein said shuttle moves with said retraction frame when connected thereto.

10. The medical assembly safety device according to claim 9 wherein said safety trigger includes a displaceable trigger latch for mating with said safety shuttle and wherein said retraction frame includes a side tab which cooperates with said trigger latch to release said safety trigger from said safety shuttle wherein forces applied by the compression spring proximally moves the safety shuttle and retraction frame to fully retract the needle and guidewire within said housing.

11. The medical assembly safety device according to claim 9 wherein said safety shuttle further comprises a shuttle tab extending therefrom for cooperating with a side tab of said retraction frame to prevent distal movement of said retraction frame.

12. The medical assembly safety device according to claim 1 wherein said external tab is removable from said retraction frame when said passive retraction system is activated.

13. The medical assembly safety device according to claim 12 wherein said upper housing includes a stripper post for stripping a portion of said external tab from said retraction frame.

14. The medical assembly safety device according to claim 1 further comprising a disc cap positioned within said housing distal to and adjacent a distal end surface of said retraction frame, said disc cap defining an aperture for removeable receipt of said needle wherein said disc cap provides a closure of said housing cavity upon retraction of said needle and guidewire.

15. The medical assembly safety device according to claim 14 wherein said housing distal end defines a groove on an inner distal end surface configured for receipt of said disc cap.

16. The medical assembly safety device according to claim 1 wherein said safety shuttle and said compression spring of said passive retraction system are proximal to said pulley assembly within said housing.

17. The medical assembly safety device according to claim 1 wherein said safety shuttle is moveably connected to said lower frame member when said passive retention system is activated.

* * * * *